United States Patent [19]
Fischer

[11] 3,933,461
[45] Jan. 20, 1976

[54] HERBICIDE
[75] Inventor: Adolf Fischer, Mutterstadt, Germany
[73] Assignee: BASF Aktiengesellschaft, Ludwigshafen Germany
[22] Filed: June 3, 1974
[21] Appl. No.: 476,150

[30] Foreign Application Priority Data
June 16, 1973 Germany............................ 2330743

[52] U.S. Cl. ........................................ 71/91; 71/88
[51] Int. Cl.² ............................................ A01D 9/14
[58] Field of Search .................................. 71/88, 91

[56] References Cited
UNITED STATES PATENTS

| | | | |
|---|---|---|---|
| 3,198,786 | 8/1965 | Tilles .................................. | 71/88 X |
| 3,224,861 | 12/1965 | D'Amico................................ | 71/88 |
| 3,708,277 | 1/1973 | Zeidler et al. ......................... | 71/91 |
| 3,708,471 | 1/1973 | Rohr et al............................ | 71/88 X |

Primary Examiner—Lewis Gotts
Assistant Examiner—Catherine L. Mills
Attorney, Agent, or Firm—Johnston, Keil, Thompson & Shurtleff

[57] ABSTRACT
New and valuable herbicides containing compositions of different active ingredients.

4 Claims, No Drawings

HERBICIDE

This application discloses and claims subject matter described in German patent application No. P 23 30 743.9, filed June 16, 1973, which is incorporated herein be reference.

The present invention relates to new and valuable herbicides containing compositions of different active ingredients.

It is known that benzothiadiazinone dioxides (German Laid-Open Application DOS 1,542,836) and hexahydro-1-H-azepine-1-carbothiolates (German Laid-Open Application DOS 1,300,947) have a herbicidal action. However, this action is not always satisfactory.

I have now found that a composition of
a. a compound of the formula

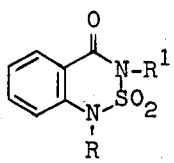

where R denotes hydrogen and $R^1$ denotes lower alkyl, or a salt thereof, e.g. ammonium, sodium, potassium, lithium, calcium, magnesium, ethylamine, dimethylamine, ethanolamine, and diethanolamine, etc., and
b. a compound of the formula

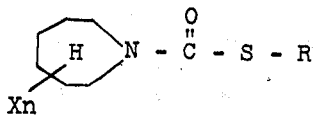

where X denotes lower alkyl, n denotes one of the integers 0, 1, 2 and 3, and R denotes lower alkyl, unsubstituted phenyl, phenyl substituted by halogen or alkyl, unsubstituted benzyl or benzyl substituted by halogen or alkyl, has a much better herbicidal action than its components.

The compositions may contain one or more compounds of the formula $a$ and of the formula $b$ in a ratio of $a:b$ of from 0.1:10 to 10:1 parts by weight.

The amount used of the agents of the invention may vary and depends in essence on the effect desired; it generally is from 0.1 to 30 and more, and preferably from 0.2 to 6, kg of active ingredient per hectare. The agents according to the invention may be applied either once or several times before or after planting, before sowing, pre- or postemergence, or during emergence of the crop plants or weeds.

The compositions are suitable for controllng unwanted plants in crops such as *Oryza sativa*, *Triticum spp.*, *Hordeum volgare*, *Secale cereale*, *Zea mays*, *Sorghum spp.*, *Soja hispida*, and *Solanum tuberosum*.

The compositions may also be used as total herbicides on ditches, aquatic areas, railway tracks and barren and waste land.

Application may be effected for instance in the form of directly sprayable solutions, powders, suspensions, dispersions, emulsions, oil dispersions, pastes, dusts, or granules by spraying, atomizing, dusting, broadcasting or watering. The forms of application depend entirely on the purpose for which the agents are being used; in any case they should ensure a fine distribution of the active ingredient.

For the preparation of solutions, emulsions, pastes and oil dispersions to be sprayed direct, mineral oil fractions of medium to high boiling point, such as kerosene or diesel oil, further coal-tar oils and oils of vegetable or mineral origin, aliphatic, cyclic and aromatic hydrocarbons such as benzene, toluene, xylene, paraffin, tetrahydronapthalene, alkylated naphthalenes, methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ether, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, broadcasting agents and dusts may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silica gel, silicic acid, silicates, talc, kaolin, Attaclay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations contain from 0.1 to 95, preferably from 0.5 to 90,% by weight of active ingredient.

There may be added (if desired, immediately before use (tankmix)) to the compositions or individual active ingredients (used singly, either before, simultaneously with and/or after the active ingredients of the invention) oils of various types, herbicides, fungicides, nematocides, insecticides, bactericides, trace elements, fertilizers, antifoams (e.g., silicones), growth regulators, antidotes and other herbicidally effective compounds such as
  substituted anilines,
  substituted aryloxycarboxylic acids and salts, esters and amides thereof,
  substituted ethers,
  substituted arsonic acids and their salts, esters and amides,
  substituted benzimidazoles,
  substituted benzisothiazoles,
  substituted benzothiadiazinone dioxides,
  substituted benzoxazines,
  substituted benzoxazinones,
  substituted benzothiadiazoles,
  substituted biurets,
  substituted quinolines,
  substituted carbamates,
  substituted aliphatic carboxylic acids and their salts, esters, and amides,
  substituted aromatic carboxylic acids and their salts, esters and amides,
  substituted carbamoylalkylthiol- or -dithiophosphates,
  substituted quinazolines,
  substituted cycloalkylamidocarbothiolic acids and their salts, esters and amides,
  substituted cycloalkylcarbonamidothiazoles,
  substituted dicarboxylic acids and their salts, esters and amides,
  substituted dihydrobenzofuranyl sulfonates,
  substituted disulfides,
  substituted dipyridylium salts,
  substituted dithiocarbamates,
  substituted dithiophosphoric acids and their salts, esters and amides,
  substituted ureas,
  substituted hexahydro-1-H-carbothioates,
  substituted hydantoins,
  substituted hydrazides,
  substituted hydrazonium salts,
  substituted isooxazole pyrimidones,
  substituted imidazoles,
  substituted isothiazole pyrimidones,
  substituted ketones,
  substituted naphthoquinones,
  substituted aliphatic nitriles,
  substituted aromatic nitriles,
  substituted oxadiazoles,
  substituted oxadiazinones,
  substituted oxadiazolidine diones,
  substituted oxadiazine diones,
  substituted phenols and their salts and esters,
  substituted phosphonic acids and their salts, esters and amides,
  substituted phosphonium chlorides,
  substituted phosphonalkylglycines,
  substituted phosphites,
  substituted phosphoric acids and their salts, esters and amides,
  substituted piperidines,
  substituted pyrazoles,
  substituted pyrazole alkylcarboxylic acids and their salts, esters and amides,
  substituted pyrazolium salts,
  substituted pyrazolium alkyl sulfates,
  substituted pyridazines,
  substituted pyridazones,
  substituted pyridine carboxylic acids and their salts, esters and amides,
  substituted pyridines,
  substituted pyridine carboxylates,
  substituted pyridinones,
  substituted pyrimidines,
  substituted pyrimidones,
  substituted pyrrolidine carboxylic acid and its salts, esters and amides,
  substituted pyrrolidines,
  substituted pyrrolidones,
  substituted arylsulfonic acids and their salts, esters and amides,
  substituted styrenes,
  substituted tetrahydrooxadiazine diones,
  substituted tetrahydrooxadiazole diones,
  substituted tetrahydromethanoindes,
  substituted tetrahydrooxadiazole thiones,
  substituted tetrahydrodiazine thiones,
  substituted tetrahydrothiadiazole diones,
  substituted aromatic thiocarbonylamides,
  substituted thiocarboxylic acids and their salts, esters and amides,
  substituted thiol carbamates,
  substituted thioureas,
  substituted thiophosphoric acids and their salts, esters and amides,
  substituted triazines,
  substituted uracils,
  substituted uretidine diones.

These agents may be added to the herbidides according to the invention in a ratio by weight of from 1:10 to 10:1. The same applies to oils, fungicides, nematocides, insecticides, bactericides, trace elements, fertilizers, antidotes and growth regulators.

The agents have a strong herbicidal action and may therefore be used as weedkillers or for controlling the growth of unwanted plants. Whether the new active ingredients are used as total or selective agents depends in essence on the amount of ingredient used per unit area.

By "weeds" and "unwanted plant growth" are meant all monocotyledonous and dicotyledonous plants which grow in loci where they are not desired.

The agents according to the invention may therefore be used for controlling for instance Gramineae, such as
  Cynodon spp.
  Digitaria spp.
  Echinochloa spp.
  Setaria spp.
  Panicum spp.
  Alopecurus spp.
  Lolium spp.
  Sorghum spp.
  Agropyron spp.
  Phalaris spp.
  Apera spp.
  Dactylis spp.
  Avena spp.
  Bromus spp.
  Uniola spp.
  Poa spp.
  Leptochloa spp.
  Brachiaria spp.
  Eleusine spp.
  Cenchrus spp.
  Eragrostis spp.
  etc.;
Cyperaceae, such as
  Carex spp.
  Cyperus spp.
  Scirpus spp.
  Eleocharis spp.
  etc.;
diotyledonous weeds, such as
  Malvaceae, e.g.,
  Abutilon theoprasti
  Sida spp.
  Malva spp.
  Hibiscus spp.
  etc.;
Compositae, such as
  Ambrosia spp.
  Lactuca spp.
  Senecio spp.
  Sonchus spp.
  Xanthium spp.
  Iva spp.
  Galinsoga spp.
  Taraxacum spp.
  Chrysanthemum spp.
  Bidens spp.
  Centaurea spp.
  Tussilago spp.
  Lapsana communis
  Tagetes spp.
  Erigeron spp.
  Anthemis spp.
  Matricaria spp.
  Artemisia spp.
  etc.;

-continued

Cirisum spp.
Convolvulaceae, such as
  Convoluvulus spp.
  Ipomoea spp.
  Jaquemontia tamnifolia
Cruciferae, such as
  Barbarea vulgaris
  Brassica spp.
  Capsella spp.
  Sisymbrium spp.
  Thalaspi spp.
  Sinapis arvensis
  Raphanus spp.
Geraniaceae, such as
  Erodium spp.
  Geranium spp.
Portulacaceae, such as
  Portulaca spp.
Primulaceae, such as
  Anagallis arvensis
  Lysimachia spp.
Rubiaceae, such as
  Richardia spp.
  Galium spp.
Scrophulariaceae, such as
  Linaria spp.
  Digitalis spp.
  Veronica spp.
Solanaceae, such as
  Physalis spp.
  Solanum spp.
  Datura spp.
Urticaceae, such as
  Urtica spp.
Violaceae, such as
  Viola spp.
Zygophyllaceae, such as
  Tribulus terrestis
Euphorbiaceae, such as
  Mercurialis annua
Umbelliferae, such as
  Daucus carota
  Aethusa cynapium
Commelinaeae, such as
  Commelina spp.
Labiatae, such as
  Lamium spp.
  Galeopsis spp.
Leguminosae, such as
  Medicago spp.
  Trifolium spp.
  Vicia spp.
  Lathyrus spp.
Plantaginaceae, such as
  Plantago spp.
Polygonaceae, such as
  Polygonum spp.
  Rumex spp.
Aizoaceae, such as
  Mollugo verticillata
Amaranthaceae, such as
  Amaranthus spp.
Boraginaceae, such as
  Amsinckia spp.
  Myostis spp.
  Lithospermum spp.
Caryophyllaceae, such as
  Stellaria spp.
  Spergula spp.
  Saponaria spp.
  Scleranthus annuus
Chenopodiaceae, such as
  Chenopodium spp.
  Kochia spp.
  Salsola kali
Lythraceae, such as
  Cuphea spp.
Oxalidaceae, such as
  Oxalis spp.
Ranunculaceae, such as
  Ranunculus spp.
  Delphinium spp.
Papaveraceae, such as
  Papaver spp.
  Fumaria officinalis
Onagraceae, such as
  Jussiaea spp.
Rosaceae, such as
  Alchemillia spp.
  Potentilla spp.
Potamogetonaceae, such as
  Potamogeton spp.
Najadaceae, such as
  Najas spp.

Cuscuta spp.
etc.;

Arabidopsis thaliana
Descurainia spp.
Draba spp.
Coronopus didymus
Ledpidium spp.
etc.;

etc.;

etc.;

etc.;

Diodia spp.
etc.;

etc.;

Nicandra spp.
etc.;

etc.;

etc.;

etc.;

Euphorbia spp.

Ammi majus
etc.

etc.;

etc.;

Sesbania exaltata
Cassia spp.
etc.;

etc.;

Fagopyrum spp.
etc.;

etc.;

etc.;

Anchusa spp.
etc.;

Silene spp.
Cerastium spp.
Agrostemma githago
etc.;

Atriplex spp.
Monolepsis nuttaliana
etc.;

etc.;

etc.;

Adonis spp.
etc.;

etc.;

etc.;

etc.;

etc.;

-continued

Marsileaceae, such as
  Marsilea quadrifolia  etc.;
Polypodiaceae, such as
  Pteridium aguilinum;
Alismataceae, such as
  Alisma spp.  etc.;
  Sagittaria sagittifolia
Equisetaceae, such as
  Equisetaceae spp.  etc.

In the greenhouse and in the open the following compounds and compositions thereof were tested on the abovementioned plants:

3-methyl-2,1,3-benzothiadiazinone-(4)-2,2-dioxide
3-ethyl-2,1,3-benzothiadiazinone-(4)-2,2-dioxide
3-propyl-2,1,3-benzothiadiazinone-(4)-2,2-dioxide
3-butyl-2,1,3-benzothiadiazinone-(4)-2,2-dioxide
3-isobutyl-2,1,3-benzothiadiazinone-(4)-2,2-dioxide
3-isopropyl-2,1,3-benzothiadiazinone-(4)-2,2-dioxide
3-isopropyl-2,1,3-benzothiadiazinone-(4)-2,2-dioxide
3-isopropyl-2,1,3-benzothiadiazinone-(4)-2,2-dioxide, sodium salt
3-isopropyl-2,1,3-benzothiadiazinone-(4)-2,2-dioxide, dimethylamine salt
3-isopropyl-2,1,3-benzothiadiazinone-(4)-2,2-dioxide, diethanolamine salt
3-sec-butyl-2,1,3-benzothiadiazinone-(4)-2,2-dioxide
3-isopropyl-2,1,3-benzothiadiazinone-(4)-2,2-dioxide, methylamine salt
3-isopropyl-2,1,3-benzothiadiazinone-(4)-2,2-dioxide, trimethylamine salt
3-isopropyl-2,1,3-benzothiadiazinone-(4)-2,2-dioxide, ethylamine salt
3-isopropyl-2,1,3-benzothiadiazinone-(4)-2,2-dioxide, diethylamine salt
3-isopropyl-2,1,3-benzothiadiazinone-(4)-2,2-dioxide, ethanolamine salt
3-isopropyl-2,1,3-benzothiadiazinone-(4)-2,2-dioxide, aniline salt
3-isopropyl-2,1,3-benzothiadiazinone-(4)-2,2-dioxide, pyridine salt
3-isopropyl-2,1,3-benzothiadiazinone-(4)-2,2-dioxide, phenylenediamine salt
3-isopropyl-2,1,3-benzothiadiazinone-(4)-2,2-dioxide, cyclohexylamine salt
3-isopropyl-2,1,3-benzothiadiazinone-(4)-2,2-dioxide, dodecylhexamethylenimine salt
3-isopropyl-2,1,3-benzothiadiazinone-(4)-2,2-dioxide, hydrazine, salt
3-isopropyl-2,1,3-benzothiadiazinone-(4)-2,2-dioxide, magnesium salt
3-isopropyl-2,1,3-benzothiadiazinone-(4)-2,2-dioxide, calcium salt
3-isopropyl-2,1,3-benzothiadiazinone-(4)-2,2-dioxide, ammonium salt
3-isopropyl-2,1,3-benzothiadiazinone-(4)-2,2-dioxide, potassium salt
3-isopropyl-2,1,3-benzothiadiazinone-(4)-2,2-dioxide, lithium salt
3-isopropyl-2,1,3-benzothiadiazinone-(4)-2,2-dioxide, sodium salt
3-isopropyl-2,1,3-benzothiadiazinone-(4)-2,2-dioxide, dimethylamine salt
3-isopropyl-2,1,3-benzothiadiazinone-(4)-2,2-dioxide, diethanolamine salt 3-sec-butyl-2,1,3-benzothiadiazinone-(4)-2,2-dioxide, sodium salt
3-sec-butyl-2,1,3-benzothiadiazinone-(4)-2,2-dioxide, dimethylamine salt
3-sec-butyl-2,1,3-benzothiadiazinone-(4)-2,2-dioxide, diethanolamine salt
3-n-butyl-2,1,3-benzothiadiazinone-(4)-2,2-dioxide, sodium salt
3-n-butyl-2,1,3-benzothiadiazinone-(4)-2,2-dioxide, dimethylamine salt
3-n-butyl-2,1,3-benzothiadiazinone-(4)-2,2-dioxide, diethanolamine salt
3-n-propyl-2,1,3-benzothiadiazinone-(4)-2,2-dioxide, sodium salt
3-n-propyl-2,1,3-benzothiadiazinone-(4)-2,2-dioxide, dimethylamine salt
3-n-propyl-2,1,3-benzothiadiazinone-(4)-2,2-dioxide, diethanolamine salt
3-ethyl-2,1,3-benzothiadiazinone-(4)-2,2-dioxide, sodium salt
3-ethyl-2,1,3-benzothiadiazinone-(4)-2,2-dioxide, dimethylamine salt
3-ethyl-2,1,3-benzothiadiazinone-(4)-2,2-dioxide, diethanolamine salt
3-methyl-2,1,3-benzothiadiazinone-(4)-2,2-dioxide, dimethylamine salt
3-methyl-2,1,3-benzothiadiazinone-(4)-2,2-dioxide, sodium salt
3-methyl-2,1,3-benzothiadiazinone-(4)-2,2-dioxide, diethanolamine salt
S-ethyl-(methylhexahydro-1-H-azepine)-1-carbothiolate
S-propyl-(methylhexahydro-1-H-azepine)-1-carbothiolate
S-isopropyl-(methylhexahydro-1H-azepine)-1-carbothiolate
S-benzyl-(methylhexahydro-1-H-azepine)-1-carbothiolate
S-ethylhexahydro-1-H-azepine-1-carbothiolate
S-ethyl-(2-methylhexahydro-1-H-azepine)-1-carbothiolate
S-ethyl-(3-methylhexahydro-1-H-azepine)-1-carbothiolate
S-ethyl-(4-methylhexahydro-1-H-azepine)-1-carbothiolate
S-propyl-(3-methylhexahydro-1-H-azepine)-1-carbothiolate
S-isopropyl-(3-methylhexahydro-1-H-azepine)-1-carbothiolate
S-isopropyl-(4-methylhexahydro-1-H-azepine)-1-carbothiolate.

The action of the above compositions corresponds to that of those in Examples 1 to 6.

EXAMPLE 1

In the open, various plants were treated at a growth height of from 0.5 to 18 cm with the following amounts of the following individual active ingredients and compositions thereof as granules:

I. 3-isopropyl-2,1,3-benzothiadiazinone-(4)-2,2-dioxide, 0.5, 1, 1.5, 2, 2.5, 3 and 4 kg per hectare;
V. S-ethyl-(methylhexahydro-1-H-azepine)-1-carbothiolate, 0.5, 1, 1.5, 2, 2.5, 3 and 4 kg per hectare;
VI. S-propyl-(methylhexahydro-1-H-azepine)-1-carbothiolate, 0.5, 1, 1.5, 2, 2.5, 3 and 4 kg per hectare;
VII. S-isopropyl-(methylhexahydro-1-H-azepine)-1-carbothiolate, 0.5, 1, 1.5, 2, 2.5, 3 and 4 kg per hectare;
VIII. S-benzyl-(methylhexahydro-1-H-azepine)-1-carbothiolate, 0.5, 1, 1.5, 2, 2.5, 3 and 4 kg per hectare;
IX S-ethylhexahydro-1-H-azepine-1-carbothiolate, 0.5, 1, 1.5, 2, 2.5, 3 and 4 kg per hectare;
I + V: 0.5 + 1.5, 1.5 + 0.5, 1 + 1, 1.5 + 1.5, 2.5 + 0.5, 0.5 + 2.5, 3 + 1 and 1 + 3 kg per hectare;
I + VI: 0.5 + 1.5, 1.5 + 0.5, 1 + 1, 1.5 + 1.5, 2.5 + 0.5, 0.5 + 2.5, 3 + 1 and 1 + 3 kg per hectare;
I + VII: 0.5 + 1.5, 1.5 + 0.5, 1 + 1, 1.5 + 1.5, 2.5 + 0.5, 0.5 + 2.5, 3 + 1 and 1 + 3 kg per hectare;
I + VIII: 0.5 + 1.5, 1.5 + 0.5, 1 + 1, 1.5 + 1.5, 2.5 + 0.5, 0.5 + 2.5, 3 + 1 and 1 + 3 kg per hectare;
I + IX: 0.5 + 1.5, 1.5 + 0.5, 1 + 1, 1.5 + 1.5, 2.5 + 0.5, 0.5 + 2.5, 3 + 1 and 1 + 3 kg per hectare.

After 2 to 3 weeks it was ascertained that the compositions had a better herbicidal action than their individual components, combined with the same good crop plant compatibility.

The results are given below:

| Active ingredient kg/ha | | | I | | | | |
|---|---|---|---|---|---|---|---|
| | 0.5 | 1 | 1.5 | 2 | 2.5 | 3 | 4 |
| Crop plant: | | | | | | | |
| Oryza sativa | 0 | 0 | 0 | 0 | 0 | 0 | 0 |
| Unwanted plants: | | | | | | | |
| Echinochloa crus-galli | 0 | 10 | 15 | 20 | 24 | 25 | 30 |
| Monochoria vaginalis | 48 | 57 | 73 | 80 | 85 | 90 | 95 |
| Alisma plantago-aquatica | 40 | 55 | 70 | 80 | 85 | 95 | 100 |
| Active ingredient kg/n | | | V | | | | |
| | 0.3 | 1 | 1.5 | 2 | 2.5 | 3 | 4 |
| Oryza sativa | 0 | 0 | 0 | 0 | 0 | 0 | 0 |
| Echinochloa crus-galli | 16 | 20 | 25 | 30 | 38 | 45 | 50 |
| Monochoria vaginalis | 3 | 10 | 18 | 27 | 34 | 40 | 45 |
| Alisma plantago-aquatica | 0 | 5 | 17 | 25 | 32 | 40 | 45 |
| Active ingredient kg/ha | | | VI | | | | |
| | 0.5 | 1 | 1.5 | 2 | 2.5 | 3 | 4 |
| Oryza sativa | 0 | 0 | 0 | 0 | 0 | 0 | 0 |
| Echinochloa crus-galli | 25 | 35 | 40 | 45 | 50 | 60 | 70 |
| Monochoria vaginalis | 3 | 10 | 23 | 32 | 38 | 45 | 52 |
| Alisma plantago-aquatica | 4 | 8 | 19 | 28 | 36 | 45 | 53 |
| Active ingredient kg/ha | | | VII | | | | |
| | 0.5 | 1 | 1.5 | 2 | 2.5 | 3 | 4 |
| Oryza sativa | 0 | 0 | 0 | 0 | 0 | 0 | 0 |
| Echinochloa crus-galli | 27 | 36 | 44 | 50 | 55 | 60 | 65 |
| Monochoria vaginalis | 0 | 3 | 7 | 15 | 26 | 35 | 40 |
| Alisma plantago-aquatica | 0 | 5 | 14 | 22 | 29 | 37 | 42 |

| Active ingredient kg/ha | 0.5 | 1 | I 1.5 | 2 | 2.5 | 3 | 4 |
|---|---|---|---|---|---|---|---|
| Active ingredient kg/ha | 0.5 | 1 | VIII 1.5 | 2 | 2.5 | 3 | 4 |
| Oryza sativa | 0 | 0 | 0 | 0 | 0 | 0 | 0 |
| Echinochloa crus-galli | 15 | 28 | 37 | 48 | 69 | 80 | 94 |
| Monochoria vaginalis | 0 | 2 | 8 | 15 | 25 | 36 | 42 |
| Alisma plantago-aquatica | 0 | 4 | 5 | 5 | 8 | 10 | 18 |
| Active ingredient kg/ha | 0.5 | 1 | IX 1.5 | 2 | 2.5 | 3 | 4 |
| Oryza sativa | 0 | 0 | 0 | 0 | 0 | 0 | 0 |
| Echinochloa crus-galli | 18 | 25 | 30 | 38 | 44 | 50 | 55 |
| Monochoria vaginalis | 4 | 10 | 20 | 27 | 35 | 40 | 45 |
| Alisma plantago-aquatica | 0 | 0 | 0 | 0 | 2 | 5 | 7 |
| Active ingredient kg/ha | 0.5+ 1.5 | I + V 1.5+ 0.5 | 1+1 | 1.5 | 0.5+ 0.5 | I + VI 1.5+ 1+1 | |
| Oryza sativa | 0 | 0 | 0 | 0 | 0 | 0 | |
| Echinochloa crus-galli | 60 | 66 | 65 | 76 | 75 | 79 | |
| Monochoria vaginalis | 100 | 100 | 100 | 100 | 100 | 97 | |
| Alisma plantago-aquatica | 92 | 100 | 97 | 95 | 100 | 96 | |
| Active ingredient kg/ha | 0.5+ 1.5 | I + VII 1.5+ 0.5 | 1+1 | 0.5+ 1.5 | I + VII 1.5+ 0.5 | 1+1 | |
| Oryza sativa | 0 | 0 | 0 | 0 | 0 | 0 | |
| Echinochloa crus-galli | 79 | 76 | 81 | 71 | 64 | 72 | |
| Monochoria vaginalis | 89 | 100 | 98 | 92 | 100 | 94 | |
| Alisma plantago-aquatica | 88 | 100 | 97 | 80 | 100 | 95 | |
| Active ingredient kg/ha | 0.5 + 1.5 | I + IX 1.5 + 0.5 | 1 + 1 | | | | |
| Oryza sativa | 0 | 0 | 0 | | | | |
| Echinochloa crus-galli | 66 | 69 | 73 | | | | |
| Monochoria vaginalis | 100 | 100 | 100 | | | | |
| Alisma plantago-aquatica | 76 | 100 | 88 | | | | |
| Active ingredient kg/ha | 1.5+ 1.5 | 2.5+ 0.5 | I + V 0.5+ 2.5 | 3+1 | 1+3 | | |
| Oryza sativa | 0 | 0 | 0 | 0 | 0 | | |
| Echinochloa crus-galli | 76 | 74 | 72 | 80 | 91 | | |
| Monochoria vaginalis | 100 | 100 | 100 | 100 | 100 | | |
| Alisma plantago-aquatica | 100 | 100 | 100 | 100 | 100 | | |
| Active ingredient kg/ha | 1.5+ 1.5 | 2.5+ 0.5 | I + VI 0.5+ 2.5 | 3+1 | 1+3 | | |
| Oryza sativa | 0 | 0 | 0 | 0 | 0 | | |
| Echinochloa crus-galli | 90 | 84 | 86 | 96 | 100 | | |
| Monochoria vaginalis | 100 | 100 | 100 | 100 | 100 | | |
| Alisma plantago-aquatica | 100 | 100 | 100 | 100 | 100 | | |
| Active ingredient kg/ha | 1.5+ 1.5 | 2.5+ 0.5 | I + VII 0.5+ 2.5 | 3+1 | 1+3 | | |
| Oryza sativa | 0 | 0 | 0 | 0 | 0 | | |
| Echinochloa crus-galli | 94 | 86 | 90 | 97 | 100 | | |
| Monochoria vaginalis | 100 | 100 | 100 | 100 | 100 | | |
| Alisma plantago-aquatica | 100 | 100 | 100 | 100 | 100 | | |
| Active ingredient kg/ha | 1.5+ 1.5 | 2.5+ 0.5 | I + VIII 0.5+ 2.5 | 3+1 | 1+3 | | |
| Oryza sativa | 0 | 0 | 0 | 0 | 0 | | |
| Echinochloa crus-galli | 86 | 74 | 100 | 88 | 100 | | |
| Monochoria vaginalis | 100 | 100 | 100 | 100 | 100 | | |
| Alisma plantago-aquatica | 100 | 100 | 84 | 100 | 99 | | |
| Active ingredient kg/ha | 1.5+ 1.5 | 2.5+ 0.5 | I + IX 0.5+ 2.5 | 3+1 | 1+3 | | |
| Oryza sativa | 0 | 0 | 0 | 0 | 0 | | |
| Echinochloa crus-galli | 81 | 77 | 80 | 85 | 97 | | |
| Monochoria vaginalis | 100 | 100 | 100 | 100 | 100 | | |
| Alisma plantago-aquatica | 100 | 100 | 77 | 100 | 96 | | |

0 = no damage
100 = complete destruction

EXAMPLE 2

In the greenhouse, various plants were treated at a growth height of from 2 to 20 cm with the following amounts of the following individual active ingredients and compositions thereof as dispersions:

I. 3-isopropyl-2,1,3-benzothiadiazinone-(4)-2,2-dioxide, 0.5, 5 and 5.5 kg per hectare;
VI. S-propyl-(methylhexahydro-1-H-azepine)-1-carbothiolate, 0.5, 5 and 5.5 kg per hectare;
I + VI: 0.5 + 5 and 5 + 0.5 kg per hectare;
and, for comparison, X. ethyl N-ethyl-N-cyclohexylthiolcarbamate; 5 and 5.5 kg per hectare;

I + X: 0.5 + 5 kg per hectare.

After 14 to 18 days it was ascertained that the composition of I + VI had better crop plant compatibility than active ingredient X and the composition of I + X, combined with the same or superior herbicidal action.

The results are given below:

VII. S-isopropyl-(methylhexahydro-1-H-azepine)-1-carbothiolate, 0.5, 1, 1.5, 2, 2.5, 3 and 4 kg per hectare;

VIII. S-benzyl-(methylhexahydro-1-H-azepine)-1-carbothiolate, 0.5, 1, 1.5, 2, 2.5, 3 and 4 kg per hectare;

IX. S-ethylhexahydro-1-H-azepine-1-carbothiolate, 0.5, 1, 1.5, 2, 2.5, 3 and 4 kg per hectare;

| Active ingredient | I | | | VI | | |
|---|---|---|---|---|---|---|
| kg/ha | 0.5 | 5 | 5.5 | 0.5 | 5 | 5.5 |
| Crop plant: | | | | | | |
| Oryza sativa | 0 | 0 | 0 | 0 | 0 | 0 |
| Unwanted plants: | | | | | | |
| Echinochloa crus-galli | 0 | 35 | 40 | 25 | 76 | 85 |
| Monochoria vaginalis | 48 | 100 | 100 | 3 | 61 | 70 |
| Alisma plantago-aquatica | 40 | 100 | 100 | 4 | 64 | 73 |
| Active ingredient | I + VI | | X | | I + X | |
| kg/ha | 0.5+5 | 5+0.5 | 5 | 5.5 | 0.5+5 | |
| Oryza sativa | 0 | 0 | 25 | 35 | 25 | |
| Echinochloa crus-galli | 100 | 98 | 75 | 80 | 100 | |
| Monochoria vaginalis | 100 | 100 | 70 | 75 | 100 | |
| Alisma plantago-aquatica | 100 | 100 | 50 | 58 | 100 | |

0 = no damage
100 = complete destruction

EXAMPLE 3

In the open, various plants were treated at a growth height of from 2 to 24 cm with the following amounts of the following individual active ingredients and compositions thereof as emulsions:

III. 3-isopropyl-2,1,3-benzothiadiazinone-(4)-2,2-dioxide, dimethylamine salt, 0.5, 1, 1.5, 2, 2.5, 3 and 4 kg per hectare;

V. S-ethyl-(methylhexahydro-1-H-azepine)-1-carbothiolate, 0.5, 1, 1.5, 2, 2.5, 3 and 4 kg per hectare;

VI. S-propyl-(methylhexahydro-1-H-azepine)-1-carbothiolate, 0.5, 1, 1.5, 2, 2.5, 3 and 4 kg per hectare;

III + V: 0.5 + 1.5, 1.5 + 0.5, 1 + 1, 1.5 + 1.5, 2.5 + 0.5, 0.5 + 2.5, 3 + 1 and 1 + 3 kg per hectare;

III + VI: 0.5 + 1.5, 1.5 + 0.5, 1 + 1, 1.5 + 1.5, 2.5 + 0.5, 0.5 + 2.5, 3 + 1 and 1 + 3 kg per hectare;

III + VII: 0.5 + 1.5, 1.5 + 0.5, 1 + 1, 1.5 + 1.5, 2.5 + 0.5, 0.5 + 2.5, 3 + 1 and 1 + 3 kg per hectare;

III + VIII: 0.5 + 1.5, 1.5 + 0.5, 1 + 1, 1.5 + 1.5, 2.5 + 0.5, 0.5 + 2.5, 3 + 1 and 1 + 3 kg per hectare;

III + IX: 0.5 + 1.5, 1.5 + 0.5, 1 + 1, 1.5 + 1.5, 2.5 + 0.5, 0.5 + 2.5, 3 + 1 and 1 + 3 kg per hectare.

After 12 to 17 days it was ascertained that the compositions had a better herbicidal action than their individual components, combined with the same good crop plant compatibility.

The results are given below:

| Active ingredient | III | | | | | | |
|---|---|---|---|---|---|---|---|
| kg/ha | 0.5 | 1 | 1.5 | 2 | 2.5 | 3 | 4 |
| Crop plant: | | | | | | | |
| Oryza sativa | 0 | 0 | 0 | 0 | 0 | 0 | 0 |
| Unwanted plants: | | | | | | | |
| Echinochloa crus-galli | 5 | 10 | 13 | 15 | 20 | 25 | 40 |
| Monochoria vaginalis | 48 | 55 | 72 | 81 | 86 | 90 | 96 |
| Alisma plantago-aquatica | 30 | 52 | 80 | 92 | 98 | 100 | 100 |
| Active ingredient | V | | | | | | |
| kg/ha | 0.5 | 1 | 1.5 | 2 | 2.5 | 3 | 4 |
| Oryza sativa | 0 | 0 | 0 | 0 | 0 | 0 | 0 |
| Echinochloa crus-galli | 16 | 20 | 25 | 30 | 38 | 45 | 50 |
| Monochoria vaginalis | 3 | 10 | 18 | 27 | 34 | 40 | 45 |
| Alisma plantago-aquatica | 0 | 5 | 17 | 25 | 32 | 40 | 45 |
| Active ingredient | VI | | | | | | |
| kg/ha | 0.5 | 1 | 1.5 | 2 | 2.5 | 3 | 4 |
| Oryza sativa | 0 | 0 | 0 | 0 | 0 | 0 | 0 |
| Echinochloa crus-galli | 25 | 35 | 40 | 45 | 50 | 60 | 70 |
| Monochoria vaginalis | 3 | 10 | 23 | 32 | 38 | 45 | 52 |
| Alisma plantago-aquatica | 4 | 8 | 19 | 28 | 36 | 45 | 53 |
| Active ingredient | VII | | | | | | |
| kg/ha | 0.5 | 1 | 1.5 | 2 | 2.5 | 3 | 4 |
| Oryza sativa | 0 | 0 | 0 | 0 | 0 | 0 | 0 |
| Echinochloa crus-galli | 27 | 36 | 44 | 50 | 55 | 60 | 65 |
| Monochoria vaginalis | 0 | 3 | 7 | 15 | 26 | 35 | 40 |
| Alisma plantago-aquatica | 0 | 5 | 14 | 22 | 29 | 37 | 42 |
| Active ingredient | VIII | | | | | | |
| kg/ha | 0.5 | 1 | 1.5 | 2 | 2.5 | 3 | 4 |
| Oryza sativa | 0 | 0 | 0 | 0 | 0 | 0 | 0 |
| Echinochloa crus-galli | 15 | 28 | 37 | 48 | 69 | 80 | 94 |
| Monochoria vaginalis | 0 | 2 | 8 | 15 | 25 | 36 | 42 |
| Alisma plantago-aquatica | 0 | 4 | 5 | 5 | 8 | 10 | 18 |
| Active ingredient | IX | | | | | | |

| Active ingredient kg/ha | 0.5 | 1 | 1.5 | III 2 | 2.5 | 3 | 4 |
|---|---|---|---|---|---|---|---|
| kg/ha | 0.5 | 1 | 1.5 | 2 | 2.5 | 3 | 4 |
| Oryza sativa | 0 | 0 | 0 | 0 | 0 | 0 | 0 |
| Echinochloa crus-galli | 18 | 25 | 30 | 38 | 44 | 50 | 55 |
| Monochoria vaginalis | 4 | 10 | 20 | 27 | 35 | 40 | 45 |
| Alisma plantago-aquatica | 0 | 0 | 0 | 0 | 2 | 5 | 7 |

| Active ingredient | III + V | | | III + VI | | |
|---|---|---|---|---|---|---|
| kg/ha | 0.5+ 1.5 | 1.5+ 0.5 | 1+1 | 0.5+ 1.5 | 1.5+ 0.5 | |
| Oryza sativa | 0 | 0 | 0 | 0 | 0 | 0 |
| Echinochloa crus-galli | 67 | 65 | 64 | 81 | 73 | 80 |
| Monochoria vaginalis | 100 | 100 | 100 | 100 | 100 | 100 |
| Alisma plantago-aquatica | 83 | 100 | 92 | 84 | 100 | 98 |

| Active ingredient | III + VII | | | III + VIII | | |
|---|---|---|---|---|---|---|
| kg/ha | 0.5+ 1.5 | 1.5+ 0.5 | 1+1 | 0.5+ 1.5 | 1.5+ 0.5 | |
| Oryza sativa | 0 | 0 | 0 | 0 | 0 | 0 |
| Echinochloa crus-galli | 85 | 75 | 81 | 78 | 62 | 72 |
| Monochoria vaginalis | 91 | 100 | 94 | 92 | 100 | 92 |
| Alisma plantago-aquatica | 79 | 100 | 92 | 69 | 100 | 91 |

| Active ingredient | III + IX | | |
|---|---|---|---|
| kg/ha | 0.5 + 1.5 | 1.5 + 0.5 | 1 + 1 |
| Oryza sativa | 0 | 0 | 0 |
| Echinochloa crus-galli | 69 | 67 | 70 |
| Monochoria vaginalis | 100 | 100 | 100 |
| Alisma plantago-aquatica | 65 | 100 | 87 |

| Active ingredient | III + V | | | | |
|---|---|---|---|---|---|
| kg/ha | 1.5+ 1.5 | 2.5+ 0.5 | 0.5+ 2.5 | 3 + 1 | 1 + 3 |
| Oryza sativa | 0 | 0 | 0 | 0 | 0 |
| Echinochloa crus-galli | 72 | 71 | 78 | 79 | 90 |
| Monochoria vaginalis | 100 | 100 | 100 | 100 | 100 |
| Alisma plantago-aquatica | 100 | 100 | 98 | 100 | 100 |

| Active ingredient | III + VI | | | | |
|---|---|---|---|---|---|
| kg/ha | 1.5+ 1.5 | 2.5+ 0.5 | 0.5+ 2.5 | 3 + 1 | 1 + 3 |
| Oryza sativa | 0 | 0 | 0 | 0 | 0 |
| Echinochloa crus-galli | 88 | 82 | 90 | 97 | 100 |
| Monochoria vaginalis | 100 | 100 | 100 | 100 | 100 |
| Alisma plantago-aquatica | 100 | 100 | 100 | 100 | 100 |

| Active ingredient | III + VII | | | | |
|---|---|---|---|---|---|
| kg/ha | 1.5+ 1.5 | 2.5+ 0.5 | 0.5+ 2.5 | 3 + 1 | 1 + 3 |
| Oryza sativa | 0 | 0 | 0 | 0 | 0 |
| Echinochloa crus-galli | 92 | 83 | 96 | 97 | 100 |
| Monochoria vaginalis | 100 | 100 | 100 | 100 | 100 |
| Alisma plantago-aquatica | 100 | 100 | 94 | 100 | 100 |

| Active ingredient | III + VIII | | | | |
|---|---|---|---|---|---|
| kg/ha | 1.5+ 1.5 | 2.5+ 0.5 | 0.5+ 2.5 | 3 + 1 | 1 + 3 |
| Oryza sativa | 0 | 0 | 0 | 0 | 0 |
| Echinochloa crus-galli | 79 | 74 | 84 | 87 | 98 |
| Monochoria vaginalis | 100 | 100 | 100 | 100 | 100 |
| Alisma plantago-aquatica | 100 | 100 | 67 | 100 | 93 |

0 = no damage
100 = complete destruction

EXAMPLE 4

In the open, various plants were treated at a growth height of from 2 to 18 cm with the following amounts of the following individual active ingredients and compositions thereof as pastes:

II. 3-isopropyl-2,1,3-benzothiadiazinone-(4)-2,2-dioxide, sodium salt, 0.5, 1, 1.5, 2, 2.5, 3 and 4 kg per hectare;

V. S-ethyl-(methylhexahydro-1-H-azepine)-1-carbothiolate, 0.5, 1, 1.5, 2, 2.5, 3 and 4 kg per hectare;

VI. S-propyl-(methylhexahydro-1-H-azepine)-1-carbothiolate, 0.5, 1, 1.5, 2, 2.5, 3 and 4 kg per hectare;

VII. S-isopropyl-(methylhexahydro-1-H-azepine)-1-carbothiolate, 0.5, 1, 1.5, 2, 2.5, 3 and 4 kg per hectare;

VIII. S-benzyl-(methylhexahydro-1-H-azepine)-1-carbothiolate, 0.5, 1, 1.5, 2, 2.5, 3 and 4 kg per hectare;

IX. S-ethylhexahydro-1-H-azepine-1-carbothiolate, 0.5, 1, 1.5, 2, 2.5, 3 and 4 kg per hectare;

II + V: 0.5 + 1.5, 1.5 + 0.5, 1.5 + 1.5, 2.5 + 0.5, 0.5 + 2.5, 3 + 1 and 1 + 3 kg per hectare;

II + VI: 0.5 + 1.5, 1.5 + 0.5, 1 + 1, 1.5 + 1.5, 2.5 + 0.5, 0.5 + 2.5, 3 + 1 and 1 + 3 kg per hectare;

II + VII: 0.5 + 1.5, 1.5 + 0.5, 1 + 1, 1.5 + 1.5, 2.5 + 0.5, 0.5 + 2.5, 3 + 1 and 1 + 3 kg per hectare;

II + VIII: 0.5 + 1.5, 1.5 + 0.5, 1 + 1, 1.5 + 1.5, 2.5 + 0.5, 0.5 + 2.5, 3 + 1 and 1 + 3 kg per hectare;

II + IX: 0.5 + 1.5, 1.5 + 0.5, 1 + 1, 1.5 + 1.5, 2.5 + 0.5, 0.5 + 2.5, 3 + 1 and 1 + 3 kg per hectare.

After 12 to 18 days it was ascertained that the compositions had a better herbicidal action than their individual components, combined with the same good crop plant compatibility.

The results are given below:

| Active ingredient kg/ha | 0.5 | 1 | 1.5 | II 2 | 2.5 | 3 | 4 |
|---|---|---|---|---|---|---|---|
| Oryza sativa | 0 | 0 | 0 | 0 | 0 | 0 | 0 |
| Echinochloa crus-galli | 5 | 15 | 20 | 24 | 25 | 30 | 40 |
| Monochoria vaginalis | 46 | 55 | 70 | 78 | 83 | 88 | 92 |
| Alisma plantago-aquatica | 26 | 50 | 72 | 83 | 90 | 97 | 100 |
| Active ingredient kg/ha | 0.5 | 1 | 1.5 | V 2 | 2.5 | 3 | 4 |
| Oryza sativa | 0 | 0 | 0 | 0 | 0 | 0 | 0 |
| Echinochloa crus-galli | 16 | 20 | 25 | 30 | 38 | 45 | 50 |
| Monochoria vaginalis | 3 | 10 | 18 | 27 | 34 | 40 | 45 |
| Alisma plantago-aquatica | 0 | 5 | 17 | 25 | 32 | 40 | 45 |
| Active ingredient kg/ha | 0.5 | 1 | 1.5 | VI 2 | 2.5 | 3 | 4 |
| Oryza sativa | 0 | 0 | 0 | 0 | 0 | 0 | 0 |
| Echinochloa crus-galli | 25 | 35 | 40 | 45 | 50 | 60 | 70 |
| Monochoria vaginalis | 3 | 10 | 23 | 32 | 38 | 45 | 52 |
| Alisma plantago-aquatica | 4 | 8 | 19 | 28 | 36 | 45 | 53 |
| Active ingredient kg/ha | 0.5 | 1 | 1.5 | VII 2 | 2.5 | 3 | 4 |
| Oryza sativa | 0 | 0 | 0 | 0 | 0 | 0 | 0 |
| Echinochloa crus-galli | 27 | 36 | 44 | 50 | 55 | 60 | 65 |
| Monochoria vaginalis | 0 | 3 | 7 | 15 | 26 | 35 | 40 |
| Alisma plantago-aquatica | 0 | 5 | 14 | 22 | 29 | 37 | 42 |
| Active ingredient kg/ha | 0.5 | 1 | 1.5 | VIII 2 | 2.5 | 3 | 4 |
| Oryza sativa | 0 | 0 | 0 | 0 | 0 | 0 | 0 |
| Echinochloa crus-galli | 15 | 28 | 37 | 48 | 69 | 80 | 94 |
| Monochoria vaginalis | 0 | 2 | 8 | 15 | 25 | 36 | 42 |
| Alisma plantago-aquatica | 0 | 4 | 5 | 5 | 8 | 10 | 18 |
| Active ingredient kg/ha | 0.5 | 1 | 1.5 | IX 2 | 2.5 | 3 | 4 |
| Oryza sativa | 0 | 0 | 0 | 0 | 0 | 0 | 0 |
| Echinochloa crus-galli | 18 | 25 | 30 | 38 | 44 | 50 | 55 |
| Monochoria vaginalis | 4 | 10 | 20 | 27 | 35 | 40 | 45 |
| Alisma plantago-aquatica | 0 | 0 | 0 | 0 | 2 | 5 | 7 |
| Active ingredient kg/ha | 0.5+1.5 | II + V 1.5+0.5 | 1+1 | 0.5+1.5 | II + VI 1.5+0.5 | 1+1 | |
| Oryza sativa | 0 | 0 | 0 | 0 | 0 | 0 | |
| Echinochloa crus-galli | 66 | 72 | 71 | 79 | 80 | 86 | |
| Monochoria vaginalis | 100 | 100 | 100 | 100 | 100 | 100 | |
| Alisma plantago-aquatica | 78 | 100 | 91 | 79 | 100 | 92 | |
| Active ingredient kg/ha | 0.5+1.5 | II + VII 1.5+0.5 | 1+1 | 0.5+1.5 | II + VIII 1.5+0.5 | 1+1 | |
| Oryza sativa | 0 | 0 | 0 | 0 | 0 | 0 | |
| Echinochloa crus-galli | 84 | 83 | 87 | 77 | 70 | 78 | |
| Monochoria vaginalis | 87 | 100 | 92 | 89 | 100 | 93 | |
| Alisma plantago-aquatica | 74 | 100 | 90 | 66 | 100 | 91 | |
| Active ingredient kg/ha | 0.5 + 1.5 | II + IX 1.5 + 0.5 | 1 + 1 | | | | |
| Oryza sativa | 0 | 0 | 0 | | | | |
| Echinochloa crus-galli | 69 | 73 | 74 | | | | |
| Monochoria vaginalis | 91 | 100 | 100 | | | | |
| Alisma plantago-aquatica | 62 | 100 | 87 | | | | |
| Active ingredient kg/ha | 1.5+1.5 | 2.5+0.5 | II + V 0.5+2.5 | 3 + 1 | 1 + 3 | | |
| Oyrza sativa | 0 | 0 | 0 | 0 | 0 | | |
| Echinochloa crus-galli | 81 | 76 | 78 | 87 | 97 | | |
| Monochoria vaginalis | 100 | 100 | 100 | 100 | 100 | | |
| Alisma plantago- aquatica | 100 | 100 | 94 | 100 | 100 | | |
| Active ingredient kg/ha | 1.5+1.5 | 2.5+0.5 | II + VI 0.5+2.5 | 3 + 1 | 1 + 3 | | |
| Oryza sativa | 0 | 0 | 0 | 0 | 0 | | |
| Echinochloa crus-galli | 96 | 86 | 91 | 97 | 100 | | |
| Monochoria vaginalis | 100 | 100 | 100 | 100 | 100 | | |
| Alisma plantago-aquatica | 100 | 100 | 98 | 100 | 100 | | |
| Active ingredient kg/ha | 1.5+1.5 | 2.5+0.5 | II + VII 0.5+2.5 | 3 + 1 | 1 + 3 | | |
| Oryza sativa | 0 | 0 | 0 | 0 | 0 | | |
| Echinochloa crus-galli | 97 | 88 | 96 | 98 | 100 | | |
| Monochoria vaginalis | 100 | 100 | 100 | 100 | 100 | | |
| Alisma plantago-aquatica | 100 | 100 | 91 | 100 | 100 | | |
| Active ingredient kg/ha | 1.5+1.5 | 2.5+0.5 | II + VIII 0.5+2.5 | 3 + 1 | 1 + 3 | | |
| Oryza sativa | 0 | 0 | 0 | 0 | 0 | | |
| Echinochloa crus-galli | 92 | 76 | 100 | 92 | 100 | | |
| Monochoria vaginalis | 100 | 100 | 100 | 100 | 100 | | |

| Active ingredient kg/ha | 0.5 | 1 | 1.5 | -continued II 2 | 2.5 | 3 | 4 |
|---|---|---|---|---|---|---|---|
| *Alisma plantago-aquatica* | 100 | 100 | 70 | 100 | 99 | | |
| Active ingredient kg/ha | 1.5+ 1.5 | 2.5+ 0.5 | II + IX 0.5+ 2.5 | 3 + 1 | 1 + 3 | | |
| *Oryza sativa* | 0 | 0 | 0 | 0 | 0 | | |
| *Echinochloa crus-galli* | 84 | 77 | 82 | 90 | 98 | | |
| *Monochoria vaginalis* | 100 | 100 | 100 | 100 | 100 | | |
| *Alisma plantago-aquatica* | 100 | 100 | 63 | 100 | 92 | | |

0 = no damage
100 = complete destruction

EXAMPLE 5

In the open, various plants were treated at a growth height of from 2 to 21 cm with the following amounts of the following individual active ingredients and compositions thereof as oil dispersions:

IV. 3-isopropyl-2,1,3-benzothiadiazinone-(4)-2,2-dioxide, diethanolamine salt, 0.5, 1, 1.5, 2, 2.5, 3 and 4 kg per hectare;

V. S-ethyl-(methylhexahydro-1-H-azepine)-1-carbothiolate, 0.5, 1, 1.5, 2, 2.5, 3 and 4 kg per hectare;

VI. S-propyl-(methylhexahydro-1-H-azepine)-1-carbothiolate, 0.5, 1, 1.5, 2, 2.5, 3 and 4 kg per hectare;

VII. S-isopropyl-(methylhexahydro-1-H-azepine)-1-carbothiolate, 0.5, 1, 1.5, 2, 2.5, 3 and 4 kg per hectare;

VIII. S-benzyl-(methylhexahydro-1-H-azepine(-1-carbothiolate, 0.5, 1, 1.5, 2, 2.5, 3 and 4 kg per hectare;

IX. S-ethylhexahydro-1H-H-azepine-1-carbothiolate, 0.5, 1, 1.5, 2, 2.5, 3 and 4 kg per hectare;

IV + V: 0.5 + 1.5, 1.5 + 0.5, 1 + 1, 1.5 + 1.5, 2.5 + 0.5, 0.5 + 2.5, 3 + 1 and 1 + 3 kg per hectare;

IV + VI: 0.5 + 1.5, 1.5 + 0.5, 1 + 1, 1.5 + 1.5, 2.5 + 0.5, 0.5 + 2.5, 3 + 1 and 1 + 3 kg per hectare;

IV + VII: 0.5 + 1.5, 1.5 + 0.5, 1 + 1, 1.5 + 1.5, 2.5 + 0.5, 0.5 + 2.5, 3 + 1 and 1 + 3 kg per hectare;

IV + VIII: 0.5 + 1.5, 1.5 + 0.5, 1 + 1, 1.5 + 1.5, 2.5 + 0.5, 0.5 + 2.5, 3 + 1 and 1 + 3 kg per hectare;

IV + IX: 0.5 + 1.5, 1.5 + 0.5, 1 + 1, 1.5 + 1.5, 2.5 + 0.5, 0.5 + 2.5, 3 + 1 and 1 + 3 kg per hectare;

After 12 to 17 days it was ascertained that the compositions had a better herbicidal action than their individual components, combined with the same good crop plant compatibility.

The results are given below:

| Active ingredient kg/ha | 0.5 | 1 | 1.5 | IV 2 | 2.5 | 3 | 4 |
|---|---|---|---|---|---|---|---|
| *Oryza sativa* | 0 | 0 | 0 | 0 | 0 | 0 | 0 |
| *Echinochloa crus-galli* | 7 | 12 | 20 | 24 | 26 | 30 | 35 |
| *Monochoria vaginalis* | 46 | 55 | 70 | 78 | 85 | 90 | 95 |
| *Alisma plantago-aquatica* | 30 | 58 | 83 | 95 | 98 | 100 | 100 |
| Active ingredient kg/ha | 0.5 | 1 | 1.5 | 2 | 2.5 | 3 | 4 |
| *Oryza sativa* | 0 | 0 | 0 | 0 | 0 | 0 | 0 |
| *Echinochloa crus-galli* | 16 | 20 | 25 | 30 | 38 | 45 | 50 |
| *Monochoria vaginalis* | 3 | 10 | 18 | 27 | 34 | 40 | 45 |
| *Alisma plantago-galli* | 16 | 20 | 25 | 30 | 38 | 45 | 50 |
| *Monochloria vaginalis* | 3 | 10 | 18 | 27 | 34 | 40 | 45 |
| *Alisma plantago-aquatica* | 0 | 5 | 17 | 25 | 32 | 40 | 45 |
| Active ingredient kg/ha | 0.5 | 1 | 1.5 | VI 2 | 2.5 | 3 | 4 |
| *Oryza sativa* | 0 | 0 | 0 | 0 | 0 | 0 | 0 |
| *Echinochloa crus-galli* | 25 | 35 | 40 | 45 | 50 | 60 | 70 |
| *Monochoria vaginalis* | 3 | 10 | 23 | 32 | 38 | 45 | 52 |
| *Alisma plantago-aquatica* | 4 | 8 | 19 | 28 | 36 | 45 | 53 |
| Active ingredient kg/ha | 0.5 | 1 | 1.5 | VII 2 | 2.5 | 3 | 4 |
| *Oryza sativa* | 0 | 0 | 0 | 0 | 0 | 0 | 0 |
| *Echinochloa crus-galli* | 27 | 36 | 44 | 50 | 55 | 60 | 65 |
| *Monochoria vaginalis* | 0 | 3 | 7 | 15 | 26 | 35 | 40 |
| *Alisma plantago-aquatica* | 0 | 5 | 14 | 22 | 29 | 37 | 42 |
| Active ingredient kg/ha | 0.5 | 1 | 1.5 | VIII 2 | 2.5 | 3 | 4 |
| *Oryza sativa* | 0 | 0 | 0 | 0 | 0 | 0 | 0 |
| *Echinochloa crus-galli* | 15 | 28 | 27 | 48 | 69 | 80 | 94 |
| *Monochoria vaginalis* | 0 | 2 | 8 | 15 | 25 | 36 | 42 |
| *Alisma plantago-aquatica* | 0 | 4 | 5 | 5 | 8 | 10 | 18 |
| Active ingredient kg/ha | 0.5 | 1 | 1.5 | IX 2 | 2.5 | 3 | 4 |
| *Oryza sativa* | 0 | 0 | 0 | 0 | 0 | 0 | 0 |
| *Echinochloa crus-galli* | 18 | 25 | 30 | 38 | 44 | 50 | 55 |
| *Monochoria vaginalis* | 4 | 10 | 20 | 27 | 35 | 40 | 45 |
| *Alisma plantago-aquatica* | 0 | 0 | 0 | 0 | 2 | 5 | 7 |
| Active ingredient kg/ha | 0.5+ 1.5 | IV + V 1.5+ 0.5 | 1+1 | 0.5+ 1.5 | IV + VI 1.5+ 0.5 | 1+1 | |

| Active ingredient kg/ha | 0.5 | 1 | IV 1.5 | 2 | 2.5 | 3 | 4 |
|---|---|---|---|---|---|---|---|
| Oryza sativa | 0 | 0 | 0 | 0 | 0 | 0 | |
| Echinochloa crus-galli | 68 | 71 | 69 | 82 | 81 | 83 | |
| Monochoria vaginalis | 100 | 100 | 100 | 100 | 100 | 100 | |
| Alisma plantago-aquatica | 83 | 100 | 98 | 85 | 100 | 100 | |
| Active ingredient | | IV + VII | | | IV + VIII | | |
| kg/ha | 0.5+ 1.5 | 1.5+ 0.5 | 1+1 | 0.5+ 1.5 | 1.5+ 0.5 | 1+1 | |
| Oryza sativa | 0 | 0 | 0 | 0 | 0 | 0 | |
| Echinochloa crus-galli | 87 | 84 | 83 | 69 | 72 | 76 | |
| Monochoria vaginalis | 88 | 100 | 92 | 89 | 100 | 93 | |
| Alisma plantago-aquatica | 79 | 100 | 97 | 70 | 100 | 96 | |
| Active ingredient | | | IV + IX | | | | |
| kg/ha | 0.5 + 1.5 | | 1.5 + 0.5 | | 1 + 1 | | |
| Oryza sativa | 0 | | 0 | | 0 | | |
| Echinochloa crus-galli | 73 | | 72 | | 74 | | |
| Monochoria vaginalis | 100 | | 100 | | 100 | | |
| Alisma plantago-aquatica | 66 | | 100 | | 94 | | |
| Active ingredient | | | IV + V | | | | |
| kg/ha | 1.5+ 1.5 | 2.5+ 0.5 | 0.5+ 2.5 | 3 + 1 | 1 + 3 | | |
| Oryza sativa | 0 | 0 | 0 | 0 | 0 | | |
| Echinochloa crus-galli | 81 | 78 | 80 | 86 | 93 | | |
| Monochoria vaginalis | 100 | 100 | 100 | 100 | 100 | | |
| Alisma plantago-aquatica | 100 | 100 | 100 | 100 | 100 | | |
| Active ingredient | | | IV + VI | | | | |
| kg/ha | 1.5+ 1.5 | 2.5+ 0.5 | 0.5+ 2.5 | 3 + 1 | 1 + 3 | | |
| Oryza sativa | 0 | 0 | 0 | 0 | 0 | | |
| Echinochloa crus-galli | 96 | 88 | 93 | 97 | 100 | | |
| Monochoria vaginalis | 100 | 100 | 100 | 100 | 100 | | |
| Alisma plantago-aquatica | 100 | 100 | 98 | 100 | 100 | | |
| Active ingredient | | | IV + VII | | | | |
| kg/ha | 1.5+ 1.5 | 2.5+ 0.5 | 0.5+ 2.5 | 3 + 1 | 1 + 3 | | |
| Oryza sativa | 0 | 0 | 0 | 0 | 0 | | |
| Echinochloa crus-galli | 98 | 89 | 97 | 98 | 100 | | |
| Monochoria vaginalis | 100 | 100 | 100 | 100 | 100 | | |
| Alisma plantago-aquatica | 100 | 100 | 94 | 100 | 100 | | |
| Active ingredient | | | IV + VIII | | | | |
| kg/ha | 1.5+ 1.5 | 2.5+ 0.5 | 0.5+ 2.5 | 3 + 1 | 1 + 3 | | |
| Oryza sativa | 0 | 0 | 0 | 0 | 0 | | |
| Echinochloa crus-galli | 82 | 77 | 100 | 93 | 100 | | |
| Monochoria vaginalis | 100 | 100 | 100 | 100 | 100 | | |
| Alisma plantago-aquatica | 100 | 100 | 74 | 100 | 100 | | |
| Active ingredient | | | IV + IX | | | | |
| kg/ha | 1.5+ 1.5 | 2.5+ 0.5 | 0.5+ 2.5 | 3 + 1 | 1 + 3 | | |
| Oryza sativa | 0 | 0 | 0 | 0 | 0 | | |
| Echinochloa crus-galli | 86 | 80 | 87 | 91 | 97 | | |
| Monochoria vaginalis | 100 | 100 | 100 | 100 | 100 | | |
| Alisma plantago-aquatica | 100 | 100 | 68 | 100 | 96 | | |

0 = no damage
100 = complete destruction

EXAMPLE 6

In the greenhouse, loamy sandy soil was filled into pots and sown with the seeds of various plants. The soil prepared in this manner was then treated with the following amounts of the following individual active ingredients and compositions thereof as granules:

I. 3-isopropyl-2,1,3-benzothiadiazinone-(4)-2,2-dioxide, 2, 2.5, 3 and 5 kg per hectare;
V. S-ethyl-(methylhexahydro-1-H-azepine)-1-carbothiolate, 2, 2.5, 3 and 5 kg per hectare;
VI. S-propyl-(methylhexahydro-1-H-azepine)-1-carbothiolate, 2, 2.5, 3 and 5 kg per hectare;
VII. S-isopropyl-(methylhexahydro-1-H-azepine)-1-carbothiolate, 2, 2.5, 3 and 5 kg per hectare;
VIII. S-benzyl-(methylhexahydro-1-H-azepine)-1-carbothiolate, 2, 2.5, 3 and 5 kg per hectare;
IX. S-ethylhexahydro-1-H-azepine-1-carbothiolate, 2, 2.5, 3 and 5 kg per hectare;
I + V: 2 + 3, 3 + 2 and 2.5 + 2.5 kg per hectare;
I + VI: 2 + 3, 3 + 2 and 2.5 + 2.5 kg per hectare;
I + VII: 2 + 3, 3 + 2 and 2.5 + 2.5 kg per hectare;
I + VIII: 2 + 3, 3 + 2 and 2.5 + 2.5 kg per hectare;
I + IX: 2 + 3, 3 + 2 and 2.5 + 2.5 kg per hectare.

After 3 to 4 weeks it was ascertained that the compositions had a better herbicidal action than their individual components, combined with the same good crop plant compatibility.

The results are given below:

| Active ingredient kg/ha | I | | | | V | | | |
| | 2 | 2.5 | 3 | 5 | 2 | 2.5 | 3 | 5 |
|---|---|---|---|---|---|---|---|---|
| Oryza sativa | 0 | 0 | 0 | 0 | 0 | 0 | 0 | 0 |
| Alisma plantago-aquatica | 10 | 15 | 21 | 28 | 5 | 10 | 15 | |

-continued

| Active ingredient kg/ha | I | | | | V | | | |
|---|---|---|---|---|---|---|---|---|
| | 2 | 2.5 | 3 | 5 | 2 | 2.5 | 3 | 5 |
| Cyperus esculentus | 18 | 26 | 30 | 70 | 30 | 40 | 70 | 30 |

| Active ingredient kg/ha | VI | | | | VII | | | |
|---|---|---|---|---|---|---|---|---|
| | 2 | 2.5 | 3 | 5 | 2 | 2.5 | 2 | 5 |
| Oryza sativa | 0 | 0 | 0 | 0 | 0 | 0 | 0 | 0 |
| Alisma plantago-aquatica | 0 | 5 | 10 | 18 | 0 | 3 | 5 | 20 |
| Cyperus esculentus | 28 | 50 | 75 | 95 | 25 | 40 | 80 | |

| Active ingredient kg/ha | VIII | | | | IX | | | |
|---|---|---|---|---|---|---|---|---|
| | 2 | 2.5 | 3 | 5 | 2 | 2.5 | 2 | 5 |
| Oryza sativa | 0 | 0 | 0 | 0 | 0 | 0 | 0 | 0 |
| Alisma plantago-aquatica | 0 | 5 | 10 | 16 | 0 | 5 | 10 | 70 |
| Cyperus esculentus | 25 | 45 | 80 | 95 | 25 | 50 | 65 | |

| Active ingredient | I + V | | | I + VI | | |
|---|---|---|---|---|---|---|
| kg/ha | 2+3 | 3+2 | 2.5+2.5 | 2+3 | 3+2 | 2.5+2.5 |
| Oryza sativa | 0 | 0 | 0 | 0 | 0 | 0 |
| Alisma plantago-aquatica | 61 | 62 | 59 | 56 | 55 | 57 |
| Cyperus esculentus | 100 | 95 | 98 | 100 | 90 | 100 |

| Active ingredient | I + VII | | | I + VIII | | |
|---|---|---|---|---|---|---|
| kg/ha | 2+3 | 3+2 | 2.5+2.5 | 2+3 | 3+2 | 2.5+2.5 |
| Oryza sativa | 0 | 0 | 0 | 0 | 0 | 0 |
| Alisma plantago-aquatica | 50 | 55 | 53 | 56 | 55 | 54 |
| Cyperus esculentus | 100 | 96 | 97 | 100 | 97 | 100 |

| Active ingredient | I + IX | | |
|---|---|---|---|
| kg/ha | 2 + 3 | 3 + 2 | 2.5 + 2.5 |
| Oryza sativa | 0 | 0 | 0 |
| Alisma plantago-aquatica | 54 | 55 | 54 |
| Cyperus esculentus | 100 | 93 | 100 |

0 = no damage
100 = complete destruction

I claim:

1. A herbicide composition containing a herbicidally effective amount of mixture of
   a. a compound having the formula

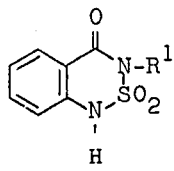

wherein $R^1$ denotes lower alkyl, or a salt of said compound, and
   b. a compound having the formula

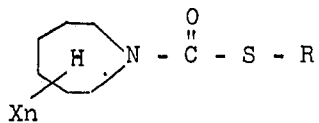

wherein X denotes lower alkyl, n denotes one of the integers 0, 1, 2 and 3, and R denotes lower alkyl, benzyl or benzyl substituted by lower alkyl in a weight ratio of a to b in the range of 5:1 to 1:5.

2. A herbicide composition as claimed in claim 1 wherein compounds a and b respectively are 3-isopropyl-2,1,3-benzothiadiazinone-(4)-2,2-dioxide and S-ethylhexahydro-1-H-azepine-1-carbothiolate.

3. A herbicide composition containing a herbicidally effective amount of a mixture of
   a. 3-isopropyl-2,1,3-benzothiadiazinone-(4)-2,2-dioxide, or a salt thereof, and
   b. a member selected from the group consisting of
      S-ethyl-(methylhexahydro-1-H-azepine)-azepine)-1-carbothiolate,
      S-propyl-(methylhexahydro-1-H-azepine)-1-carbothiolate,
      S-isopropyl-(methylhexahydro-1-H-azepine)-1-carbothiolate,
      S-benzyl-(methylhexahydro-1-H-azepine)-1-carbothiolate, and
      S-ethylhexahydro-1-H-azepine-1-carbothiolate
   in a weight ratio of a to b in the range of 5:1 to 1:5.

4. A herbicide composition as claimed in claim 3 wherein said salt of compound a is the ammonium, sodium, potassium, lithium, calcium, magnesium, ethylamine, dimethylamine, ethanolamine, or diethanolamine salt.

* * * * *

UNITED STATES PATENT AND TRADEMARK OFFICE
CERTIFICATE OF CORRECTION

PATENT NO. : 3,933,461
DATED : January 20, 1976
INVENTOR(S) : Adolf Fischer

It is certified that error appears in the above-identified patent and that said Letters Patent are hereby corrected as shown below:

In Column 1, Line 56, delete " ...Hordeum volgare,... " and substitute -- ...Hordeum vulgare,... --

In Column 9, the heading for the third table, delete

" Active ingredient         I + V                    I+VI     "
   kg/ha         0.5+      1.5+            0.5+      1.5+
   1.5           0.5       1+1      1.5    0.5       1+1 and substitute

-- Active ingredient        I+V                      I+VI              --
   kg/ha         0.5+      1.5+     1+1    0.5+      1.5+     1+1
                 1.5        0.5             1.5       0.5

In Column 18, Table V, delete "Alisma plantago-galli and the corresponding data" and delete "Monochloria vaginalis and the corresponding data"(second occurence)

In Column 20, the Table at the bottom of the column should read

-- Active ingredient                           V              --
   kg/ha         ......................        3       5
   Oryza sativa                                0       0
   Alisma plantago-aquatica                   15      23

UNITED STATES PATENT AND TRADEMARK OFFICE
CERTIFICATE OF CORRECTION

PATENT NO. : 3,933,461
DATED : January 20, 1976
INVENTOR(S) : Adolf Fischer

It is certified that error appears in the above-identified patent and that said Letters Patent are hereby corrected as shown below:

In Column 21, the Table at the top of the column should read

--Active ingredient V --

| kg/ha | 3 | 5 |
|---|---|---|
| Cyperus esculentus | 70 | 90 |

| Active ingredient | VII | |
|---|---|---|
| kg/ha | 2 | 5 |
| Oryza sativa | 0 | 0 |
| Alisma plantago-aquatica | 5 | 12 |
| Cyperus esculentus | 80 | 90 |

| Active ingredient | IX | |
|---|---|---|
| kg/ha | 2 | 5 |
| Oryza sativa | 0 | 0 |
| Alisma plantago-aquatica | 10 | 17 |
| Cyperus esculentus | 65 | 80 |

Signed and Sealed this

Twenty-eighth Day of September 1976

[SEAL]

Attest:

RUTH C. MASON
*Attesting Officer*

C. MARSHALL DANN
*Commissioner of Patents and Trademarks*